United States Patent [19]

Grollier et al.

[11] Patent Number: 5,000,937

[45] Date of Patent: Mar. 19, 1991

[54] TRANSPARENT COSMETIC COMPOSITION THAT REFLECTS INFRARED RADIATION AND ITS USE FOR PROTECTING THE HUMAN EPIDERMIS AGAINST INFRARED RADIATION

[75] Inventors: Jean F. Grollier, Paris; Georges Rosenbaum, Asnières; Jean Cotteret, Verneuil-sur-Seine, all of France

[73] Assignee: L'Oreal, Paris, France

[21] Appl. No.: 263,423

[22] Filed: Oct. 27, 1988

[30] Foreign Application Priority Data

Oct. 28, 1987 [LU] Luxembourg ............................ 87030

[51] Int. Cl.$^5$ .................... A61K 7/42; A61K 7/44; A61K 9/07; A61K 9/12
[52] U.S. Cl. ............................... 424/47; 424/DIG. 5; 424/59; 424/60; 514/844; 514/847; 514/937; 514/944; 514/969
[58] Field of Search ............................. 424/59, 60, 47

[56] References Cited

U.S. PATENT DOCUMENTS

| | | | |
|---|---|---|---|
| 4,486,405 | 12/1984 | Klein | 424/60 |
| 4,820,508 | 4/1989 | Wortzman | 424/60 |
| 4,828,825 | 5/1989 | Weber et al. | 424/60 |

FOREIGN PATENT DOCUMENTS

| | | | |
|---|---|---|---|
| 47566 | 10/1971 | Australia | 424/60 |
| 2533497 | 7/1975 | Fed. Rep. of Germany | 424/60 |
| 0227813 | 12/1984 | Japan | 514/63 |
| 0130653 | 7/1985 | Japan | 424/60 |
| 0149517 | 7/1985 | Japan | 424/60 |
| 2090526 | 7/1982 | United Kingdom | 424/60 |

OTHER PUBLICATIONS

Patent Abstracts of Japan, vol. 11, No. 379 (C-463) [2826], Dec. 10, 1987; & JP-A-62 149 613 (Max Fuakutaa K.K.), 03-07-1987.
Patent Abstracts of Japan, vol. 11, No. 176 (C-426) [2623], Jun. 5, 1987; & JP-A-62 4212 (Catalysts & Chem. Ind. Co. Ltd.), 10-01-1987.
Patent Abstracts of Japan, vol. 9, No. 96 (C-278) [1819], Apr. 25, 1985; & JP-A-59 227 813 (Sumitomo Kagaku Kogyo K.K.), 21-12-1984.

*Primary Examiner*—Dale R. Ore
*Attorney, Agent, or Firm*—Marshall, O'Toole, Gerstein, Murray & Bicknell

[57] ABSTRACT

Transparent cosmetic composition that reflects infrared radiation and its use for protecting the human epidermis against infrared radiation.

The invention relates to a transparent cosmetic composition comprising, by way of an agent that reflects infrared radiation for protecting the human epidermis, a substance which is dispersible in the cosmetic medium used, possessing a reflectance (R) of infrared radiation equal to at least 45%, and of which a 2% strength dispersion in vaseline possesses an optical transmission in the visible of at least 85%, chosen from a diatom of particle size less than 100 microns, hollow glass microspheres of size less than 100 microns, a bismuth oxychloride of particle size less than 75 microns and zirconium powder covered ceramic microparticles of particle size less than 8 microns.

This cosmetic composition can also contain 0.5 to 20% by weight of UV-A, UV-B or broad-band screening agents.

23 Claims, No Drawings

TRANSPARENT COSMETIC COMPOSITION THAT REFLECTS INFRARED RADIATION AND ITS USE FOR PROTECTING THE HUMAN EPIDERMIS AGAINST INFRARED RADIATION

The present invention relates to a transparent cosmetic composition containing new substances by way of reflectors of infrared radiation, as well as to the use of the said cosmetic composition for protecting the human epidermis against infrared radiation.

The importance of ultraviolet radiation in the tanning of the human epidermis, but also in skin ageing, and in particular that of erythemogenic UV-B rays of wavelengths between 280 and 320 nm, which are the main cause of photocarcinogenesis, is known. It has also been demonstrated recently that UV-A rays, of wavelengths between 320 and 400 nm, which cause tanning of the skin, increase the harmful effects of UV-B (The Journal of Investigative Dermatology, Vol. 59, No. 6, page 416, 1973, J. Willis, A. Kligman and J. Epstein).

However, solar radiation reaching the earth's surface also comprises 40% of a not insignificant radiation, namely infrared radiation, of wavelengths between approximately 760 and 2,500 nm.

The incidence of infrared radiation on the human epidermis is hence naturally closely linked to exposure to sun, but also to the lamps used in hairdressing salons for the natural drying of the hair, as well as to the current return of heating with wood.

Recent studies published by Lorraine H. KLIGMAN of the University of Pennsylvania, U.S.A., in the journal Arch. Dermatol. Res. 1982, 272, pages 229–238, demonstrate that infrared radiation, although physiologically pleasant, is not harmless and that it gives rise, by itself, in the upper dermis, to a dense multiplication of fine elastic fibres resembling a nap, referred to as elastosis, and a thickening of the fibres capable of inducing carcinogenesis.

Infrared radiation causes, in addition, a vasodilation and a rise in the skin temperature, resulting in a skin erythema designated "erythema ab igne" in L. H. Kligman's publication.

It has hence proved especially advantageous to reflect the infrared radiation in order to attenuate its harmful effects on the human epidermis.

The property of reflecting natural radiation, possessed by certain opaque pigments, is known. Among these pigments, metal salt and oxide powders, such as titanium dioxide and zinc oxide powders, may be mentioned by way of example.

However, when used as reflecting agents in cosmetic compositions that protect the human epidermis, metal salt and oxide powders have the drawback of forming an unattractive white film on the skin.

The Applicant has hence performed many investigations for the purposes of discovering new substances which, when introduced into a cosmetic composition, make it possible both to reflect satisfactorily the infrared radiation capable of damaging the human epidermis, and to obtain protective cosmetic compositions which, after application, do not leave a white film, disliked by the user, remaining on the skin, which are not sticky to the touch and which show good adhesion to the skin as well as good chemical and photochemical stability.

The Applicant has thus discovered that certain substances, dispersible in the cosmetic medium in which they are used, possessing a reflectance (R) of infrared radiation equal to at least 45%, and preferably to 55%, and of which a 2% strength dispersion in vaseline possesses an optical transmission in visible light of at least 85%, and preferably at least 90%, could, surprisingly, both reflect infrared radiation and endow the cosmetic compositions containing them with the desired advantageous properties stated above, and especially transparency on the human epidermis, good adhesion to the skin and good chemical and photochemical stability, as well as an effect of attenuation of the erythema "ab igne" caused by infrared radiation.

The subject of the invention is hence a transparent cosmetic composition that protects the human epidermis against infrared radiation comprising, in a cosmetically acceptable vehicle, an effective amount of at least one substance as defined above, chosen from:
  a diatom of particle size less than 100 microns, and preferably less than 80 microns;
  hollow glass microspheres of size less than 100 microns, and preferably less than 80 microns;
  a bismuth oxychloride of particle size less than 75 microns, and preferably less than 40 microns; and
  zirconium powder covered ceramic microparticles of particle size less than 8 microns.

The subject of the invention is, in addition, a process for protecting the human epidermis against infrared radiation, consisting in applying on the skin a sufficient amount of a cosmetic composition comprising at least one substance as defined above, by way of an infrared-reflecting agent.

Especially preferred infrared-reflecting agents for use according to the invention are:
  a diatom of particle size between 5 and 80 microns, sold by Société Bretonne de Produits Chimiques et Pharmaceutiques under the name "CLARSEL DIC/B";
  hollow glass microspheres of size less than 75 microns, sold by the company 3M under the name "Glass microspheres E 22 X";
  a bismuth oxychloride of average particle size 6 to 15 microns, sold by the company MALLINCKRODT under the name "PEARL GLO"; and
  zirconium powder covered ceramic microparticles possessing a particle size of 4 to 5 microns, sold by the company TORAY under the name "TORAYCERAM", for example "TORAYCERAM ZP 550" and "TORAYCERAM ZP 4000".

The higher the reflectance (R) of the infrared-reflecting agent, the more effective the latter.

The reflectance is the ratio between the intensity of the reflected flux and the intensity of the incident flux. This measurement is performed in the wavelength region ranging from 1,100 to 2,500 nm, using an apparatus known as "Infra-alyseur".

The optical transmission in the visible of a 2% strength dispersion of reflecting agent in vaseline is measured by means of a spectrophotometer with an integration sphere in the wavelength region ranging from 400 to 700 nm, using thin, approximately 10μ, layers.

The optical transmission is the ratio between the intensity of the transmitted flux and the intensity of the incident flux.

The infrared-reflecting agent or agents according to the invention is/are present in the cosmetic composition that protects the human epidermis in proportions of between 0.5 and 20% by weight, and preferably between 1 and 10% by weight, and still better between 1 and 3% by weight, relative to the total weight of the composition.

The cosmetic compositions containing the infrared-reflecting agent according to the invention can also contain agents that screen ultraviolet radiation which are well known in the prior art and compatible with the infrared-reflecting agents used according to the invention. These agents that screen ultraviolet radiation can be lipid-soluble or water-soluble UV-A, UV-B or broadband screening agents.

They are present in the cosmetic compositions according to the invention in proportions of between 0.5 and 20% by weight relative to the total weight of the composition.

By way of UV screening agents capable of being used in the transparent cosmetic composition according to the invention, the following compounds may be mentioned, this list not being limitative:

para-aminobenzoic acid, its esters and derivatives such as:
Ethyl N,N-dihydroxypropyl-para-aminobenzoate
Ethyl N-ethoxy-para-aminobenzoate
Ethyl para-dimethylaminobenzoate
Amyl para-dimethylaminobenzoate
Glyceryl para-aminobenzoate
Butyl para-dimethylaminobenzoate
2-Ethylhexyl para-dimethylaminobenzoate
the following salicylates:
Potassium or triethanolamine salicylate
Amyl salicylate
Menthyl salicylate
Homomenthyl salicylate
2-Ethylhexyl salicylate
Phenyl salicylate
Benzyl salicylate
para-Isopropanolphenyl salicylate
Isodecyl salicylate
Homomenthyl N-acetylanthranilate
The following cinnamates and cinnamic acid derivatives:
Potassium cinnamate
Octyl cinnamate
Ethyl 4-isopropyl cinnamate
Ethyl 2,4-diisopropyl cinnamate
Methyl 2,4-diisopropyl cinnamate
para-Methoxycinnamic acid and its salts
Propyl para-methoxy cinnamate
Isopropyl para-methoxy cinnamate
Isoamyl para-methoxy cinnamate
2-Ethylhexyl para-methoxy cinnamate
2-Ethoxyethyl para-methoxy cinnamate
Cyclohexyl para-methoxy cinnamate
Ethyl α-cyano-β-phenyl cinnamate
2-Ethylhexyl α-cyano-β-phenyl cinnamate
The following benzophenones:
2,4-Dihydroxybenzophenone
2,2'-Dihydroxy-4-methoxybenzophenone
2,2'-Dihydroxy-4,4'-dimethoxybenzophenone
2,2'-Dihydroxy-4,4'-dimethoxybenzophenone-5-sulphonic acid and its salts
2,2',4,4'-Tetrahydroxybenzophenone
2-Hydroxy-4-methoxybenzophenone
2-Hydroxy-4-methoxy-4'-methylbenzophenone
2-Hydroxy-4-methoxybenzophenone-5-sulphonic acid and its salts
4-Phenylbenzophenone
2-Ethylhexyl 4'-phenylbenzophenone-2-carboxylate
2-Hydroxy-4-n-octyloxybenzophenone
4-Hydroxy-3-benzophenonecarboxylic acid and its salts
2-Phenylbenzimidazole-5-sulphonic acid and its salts
Urocanic acid and its salts
Ethyl urocanate
2-Phenyl-5-methylbenzoxazole
2-(2'-Hydroxy-5'-methylphenyl)benzotriazole
2-(2'-Hydroxy-5'-tert-octylphenyl)benzotriazole
Sodium 3,4-dimethoxyphenylglyoxylate
Dibenzalazine
Dianisoylmethane
4-Isopropyldibenzoylmethane
4-tert-Butyl-4'-methoxydibenzoylmethane
3-Benzylidene-dl-camphor
3-(4'-Methylbenzylidene)-dl-camphor
3-(4'-Sulphobenzylidene)camphoric acid and its salts (French Patent No. 2,282,426)
3-(3'-Sulpho-4'-methylbenzylidene)camphoric acid and its salts (French Patent No. 2,236,515)
4-(2-Oxo-3-bornylidenemethyl)phenyltrimethylammonium methyl sulphate (French Patent No. 2,199,971)
Methyleugenol
Guanine
Digalloyl trioleate
5-(3,3-Dimethyl-2-norbornylidene)-3-penten-2-one
Benzene-1,4-bis(3-methylidene-10-camphorsulphonic) acid and its salts (French Patent No. 2,528,420)
N-(2-Ethylhexyl)-4-(3'-methylidenecamphor)benzenesulphonamide (French Patent No. 2,529,887)
N-(2-Ethylhexyl)-3-[(3'-methoxy-4'-n-butoxy)benzylidene]-10-camphorsulphonamide (French Patent No. 2,529,887)
N-(2-Ethylhexyl)-3-benzylidene-10-camphorsulphonamide (French Patent No. 2,529,887)
the homopolymer of 3-[4'-(acrylamidomethyl)benzylidene]-dl-camphor of MW less than 20,000 (French Patent No. 2,601,365)
the copolymer of 2-[(2'-hydroxy-5'-tert-octyl)phenyl]-2H-benzotriazole and butyl vinyl ether (French Patent No. 2,601,365)

The cosmetic composition according to the invention may be presented in the form of a suspension or dispersion in solvents or fats, in the form of an emulsion such as a cream or a milk, or in the form of an ointment, a gel or a solid stick, or may be packaged as an aerosol and be presented in the form of a foam.

It can contain the cosmetic adjuvants usual in this type of composition, such as thickeners, emollients, moisturizing products, surfactants, preservatives, sequestering agents, antioxidants, antifoams, oils, waxes, lanolin, perfumes, propellents, colorants, vitamins or any other ingredient customarily used in cosmetics.

In the case of a composition packaged as an aerosol, traditional propellents such as alkanes, fluoroalkanes and chlorofluoroalkanes are used.

Among the main adjuvants capable of being present in the cosmetic compositions of the invention, there may be mentioned solvents such as water and lower monohydric alcohols or polyols containing 1 to 6 carbon atoms, or mixtures thereof, especially preferred monohydric alcohols or polyols being ethanol, isopropanol, propylene glycol, glycerin and sorbitol; there may also be mentioned fats such as mineral, animal, vegetable or synthetic oils or waxes, fatty acids, fatty acid esters such as triglycerides of fatty acids having from 6 to 12 carbon atoms, fatty alcohols, vaseline, paraffin, lanolin, hydrogenated lanolin, acetylated lanolin and silicone oil.

An embodiment of the invention is an emulsion in the form of a cream or milk comprising, in addition to the infrared-reflecting agent, fatty alcohols, fatty acid esters and in particular fatty acid triglycerides, fatty acids, lanolin and its derivatives, natural or synthetic oils or waxes, and emulsifiers, in the presence of water.

A preferred embodiment of the invention is a water-in-oil type emulsion.

An emulsion of this kind contains an aqueous phase, a fatty phase and an emulsifying system.

In this type of emulsion, the concentration of emulsifying system is between 4 and 35% relative to the total weight of the emulsion; the fatty phase is present in proportions of between 20 and 60% and the aqueous phase in proportions of between 20 and 70%, relative to the total weight of the emulsion. The emulsifiers are those customarily used in this type of emulsion. They are more especially chosen from:

fatty acid ($C_{12}$–$C_{18}$) esters of sorbitan;

esters of hydroxystearic acid and fatty alcohols ($C_{12}$–$C_{30}$);

mono- and diesters of fatty acids ($C_{12}$–$C_{18}$) and glycerol or polyglycerol;

condensates of ethylene oxide with propylene glycols;

oxypropylenated/oxyethylenated fatty alcohols ($C_{12}$–$C_{20}$);

polycyclic alcohols such as sterols;

high molecular weight aliphatic alcohols such as lanolin mixtures of oxypropylenated/polyglycerolated alcohols and magnesium isostearate;

succinic esters of polyoxyethylenated or polyoxypropylenated fatty alcohols; and mixtures of magnesium lanolate, calcium lanolate, lithium lanolate, zinc lanolate or aluminium lanolate and lanolin alcohol or hydrogenated lanolin.

Among fatty products forming the fatty phase of the emulsions, there may be mentioned:

hydrocarbon oils such as paraffin oil, purcellin oil, perhydrosqualene and solutions of microcrystalline waxes in oils, animal or vegetable oils such as sweet almond oil, avocado oil, oil of calophyllum, lanolin and its derivatives, castor oil, caballine oil, pig oil, sesame oil, olive oil, jojoba oil, shea oil, hoplostethus oil, mineral oils whose initial distillation point at atmospheric pressure is approximately 250° C. and whose final point is of the order of 410° C., such as liquid paraffin, saturated or unsaturated fatty acid esters, such as alkyl myristates, such as isopropyl, butyl or cetyl myristate, hexadecyl stearate, ethyl or isopropyl palmitates, triglycerides of octanoic and decanoic acids and cetyl ricinoleate.

The fatty phase can also contain silicone oils which are soluble in other oils, such as dimethylpolysiloxane, methylphenylpolysiloxane and silicone/glycol copolymer, fatty acids and fatty alcohols.

For the purpose of promoting oil retention, it is also possible to use waxes such as carnauba wax, candelilla wax, beeswax, microcrystalline wax, ozokerite and Ca, Mg and Al oleates, myristates, linoleates and stearates.

The emulsions of the water-in-oil type may also be presented in the form of sun sticks. In this case, the concentration of the aqueous phase in the emulsion is generally between 5 and 70% by weight, relative to the total weight of the emulsion.

In general, these water-in-oil emulsions are prepared by introducing the fatty phase and the emulsifier into the manufacturing tank. The mixture is heated to a temperature of 70°–75° C. The oil-soluble ingredients are then added, after which the water, brought beforehand to the same temperature, in which the water-soluble ingredients have been dissolved beforehand is added with stirring; the mixture is stirred until an emulsion having the desired fineness is obtained, and then allowed to cool to room temperature, optionally with slow stirring.

The fatty gels comprise an oil or wax and a thickener such as silica. The oleo-alcoholic or aqueous-alcoholic gels comprise one or more lower alcohols or polyols such as ethanol, propylene glycol or glycerin, a thickener such as silica, cellulose derivatives, polyacrylic acid derivatives, and guar, carob and xanthan gums, in the presence of oil or water, respectively.

The solid sticks consist of fats such as natural or synthetic waxes and oils, fatty alcohols, fatty acid esters and lanolin.

The examples which follow are designed to illustrate the invention, no limitation of the latter being implied.

EXAMPLE 1

A transparent cream that protects the human epidermis is prepared in the form of a water-in-oil emulsion, of the following composition:

| | |
|---|---|
| 2-Octyl-1-dodecanol | 10 g |
| Magnesium stearate | 4 g |
| Beeswax | 5 g |
| Hydrogenated lanolin | 1 g |
| Lanolin | 4 g |
| Sorbitan sesquioleate sold by the company ICI under the name "ARLACEL 83" | 4.5 g |
| Mixture of glycerol mono- and distearate and potassium stearate | 1 g |
| Liquid paraffin | 27 g |
| Diatomite sold by the company SOBREP under the name "CLARSEL DIC/B" | 2 g |
| Imidazolidinylurea derivative sold by the company SUTTON Labs under the name "GERMALL 115" | 0.2 g |
| Perfume | qs |
| Water | qs 100 g |

This cream is prepared according to traditional techniques for preparing emulsions, by dispersing the infrared-reflecting agent in the fats and the emulsifiers, heating this fatty phase to about 70°–75° C. and adding the water, also heated to 70°–75° C., with brisk stirring; stirring is maintained for 10 to 15 minutes, the mixture is then allowed to cool with moderate stirring and, at about 40° C., perfume and preservative are added.

EXAMPLE 2

As in Example 1, a transparent cream that protects the human epidermis is prepared in the form of a water-in-oil emulsion having the following compositions:

| | |
|---|---|
| 2-Octyl-1-dodecanol | 10 g |
| Magnesium stearate | 4 g |
| Beeswax | 5 g |
| Hydrogenated lanolin | 1 g |
| Lanolin | 4 g |
| Sorbitan sesquioleate sold by the company ICI under the name "ARLACEL 83" | 4.5 g |
| Mixture of glycerol mono- and distearate and potassium stearate | 1 g |
| Liquid paraffin | 27 g |

| -continued | |
|---|---|
| Hollow glass microspheres sold by the company 3M under the name "GLASS MICROSPHERES E 22 X" | 2 g |
| Imidazolidinylurea derivative sold by the company SUTTON Labs under the name "GERMALL 115" | 0.2 g |
| Perfume | qs |
| Water | qs 100 g |

EXAMPLE 3

A transparent cream that protects the human epidermis is prepared in the form of a water-in-oil emulsion of the following composition:

| | |
|---|---|
| 2-Octyl-1-dodecanol | 10 g |
| Magnesium stearate | 4 g |
| Beeswax | 5 g |
| Hydrogenated lanolin | 1 g |
| Lanolin | 4 g |
| Sorbitan sesquioleate sold by the company ICI under the name "ARLACEL 83" | 4.5 g |
| Mixture of glycerol mono- and distearate and potassium stearate | 1 g |
| Liquid paraffin | 27 g |
| Ceramic microparticles covered with zirconium powder, sold by the company TORAY under the name "TORAYCERAM ZP 550" | 2 g |
| Imidasolidinylurea derivative sold by the company SUTTON Labs under the name "GERMALL 115" | 0.2 g |
| Perfume | qs |
| Water | qs 100 g |

EXAMPLE 4

A transparent cream that protects the human epidermis is prepared in the form of a water-in-oil emulsion of the following composition:

| | |
|---|---|
| 2-Octyl-1-dodecanol | 10 g |
| Magnesium stearate | 4 g |
| Beeswax | 5 g |
| Hydrogenated lanolin | 1 g |
| Lanolin | 4 g |
| Sorbitan sesquioleate sold by the company ICI under the name "ARLACEL 83" | 4.5 g |
| Mixture of glycerol mono- and distearate and potassium stearate | 1 g |
| Liquid paraffin | 27 g |
| Bismuth oxychloride sold by the company MALLINCKRODT under the name "PEARL GLO" | 2 g |
| Imidazolidinylurea derivative sold by the company, SUTTON Labs under the name "GERMALL 115" | 0.2 g |
| Perfume | qs |
| Water | qs 100 g |

EXAMPLE 5

A transparent cream that protects the human epidermis is prepared in the form of an oil-in-water emulsion, in the form of the following composition:

| | |
|---|---|
| Mixture of cetyl/stearyl alcohol and cetyl/ stearyl alcohol oxyethylenated with 33 moles of ethylene oxide, sold by the company HENKEL under the name "SINNOWAX AO" | 7 g |
| Mixture of non-self-emulsifying glycerol mono- and distearate | 2 g |
| Cetyl alcohol | 1.5 g |
| Silicone oil | 1.5 g |
| Liquid paraffin | 15 g |
| 4-(2-oxa-3-bornylidenemechyl)phenyltrimethylammonium methyl sulphate, prepared according to Example 1 of French Patent 2,199,971 | 2 g |
| Sodium lactate | 4 g |
| Ceramic microparticles covered with zirconium powder, sold by the company TORAY under the name "TORAYCERAM ZP 550" | 2 g |
| Glycerin | 20 g |
| Preservative, perfume | qs |
| Water | qs 100 g |

The "TORAYCERAM ZP 550" is dispersed in the fatty phase containing the emulsifier. The aqueous phase containing the water, the glycerin, the sodium lactate and the 4-(2-oxo-3-bornylidenemethyl)phenyl-trimethylammonium methyl sulphate is heated to 70°-75° C. The fatty phase, heated beforehand to 70°-75° C., is added with brisk stirring to the aqueous phase, and the mixture is then left to cool with moderate stirring; perfume and preservative are added at about 40° C.

EXAMPLE 6

A gel is prepared which is transparent on the skin, having the following composition:

| | |
|---|---|
| Diacom sold by the company SOBREP under the name "CLARSEL DIC/B" | 2 g |
| 2-Hydroxy-4-methoxybenzophenone-5-sulphonic acid (BASE UVINUL MS 40) | 0.5 g |
| Crosslinked polyacrylic acid, MW 4,000,000, sold by the company GOODRICH under the name "CARBOPOL 940" | 0.3 g |
| Propylene glycol | 30 g |
| Triethanolamine | 0.9 g |
| Sequestering agent, preservative, perfume | qs |
| Water | qs 100 g |

EXAMPLE 7

A transparent protective cream is prepared in the form of an oil-in-water emulsion, of the following composition:

| | |
|---|---|
| Mixture of cetyl/stearyl alcohol and cetyl/ stearyl alcohol oxyethylenated with 33 moles of ethylene oxide, sold by the company HENKEL under the name "SINNOWAX AO" | 7 g |
| Mixture of non-self-emulsifying glycerol mono- and distearate | 2 g |
| Cetyl alcohol | 1.5 g |
| Silicone oil | 1.5 g |
| Liquid paraffin | 15 g |
| 2-Ethylhexyl p-(dimetrylamino)benzoate | 2.5 g |
| 2-Hydroxy-4-methoxyberzophenone | 1 g |
| Diatom sold by the company SOBREP under the name "CLARSEL DIC/B" | 2 g |
| Glycerin | 20 g |
| Preservative, perfume | qs |
| Water | qs 100 g |

We claim:

1. Transparent cosmetic composition for protecting the human epidermis against infrared radiation, which comprises, in a cosmetically acceptable vehicle, an effective amount of at least one substance that reflects infrared radiation, dispersable in said vehicle, possessing a reflectance (R) of infrared radiation equal to at least 45%, and of which a 2% strength dispersion in vaseline possesses an optical transmission in the visible of at least 85%, selected from the group consisting of diatomite, hollow glass microspheres of particle size less than 100 microns, bismuth oxychloride of particle size less than 75 microns, and zirconium powder-covered ceramic microparticles of particle size less than 8 microns.

2. Transparent cosmetic composition according to claim 1, which comprises a substance that reflects infrared radiation, of which the reflectance (R) of infrared radiator is equal to at least 55% and of which a 2% strength dispersion in vaseline possesses an optical transmission in the visible of at least 90%.

3. Transparent cosmetic composition according to claim 1, wherein said infrared-reflecting substance is selected fron the group consisting of diatomite, hollow glass microspheres of particle size less than 75 microns, bismuth oxychloride of average particle size from 6 to 15 microns and zirconium powder-covered ceramic microparticles possessing a particle size of 4 to 5 microns.

4. Transparent cosmetic composition according to claim 1, which contains 0.5 to 20%, relative to the total weight of the composition, of at least one infrared-reflecting agent as defined in claim 1.

5. Transparent cosmetic composition according to claim 4, which contains 1 to 10% by weight, based on the total weight of the composition, of at least one infrared-reflecting agent as defined in claim 1.

6. Transparent cosmetic composition according to claim 5, which contains 1 to 3% by weight, based on the total weight of the composition, of at least one infrared-reflecting agent as defined in claim 1.

7. Transparent cosmetic composition according to claim 1, which further contains UV-screening agents consisting of lipid-soluble or water-soluble UV-A, UV-B or broad-band screening agents which are compatible with the infrared-reflecting agents defined above.

8. Transparent cosmetic composition according to claim 7, which contains 0.5 to 20% by weight, relative to the total weight of the composition, of at least one UV-A, UV-B or broad-band screening agent.

9. Transparent cosmetic composition according to claim 8, which contains at least one UV-screening agent selected from the group consisting of p-aminobenzoic acid and its esters, salicylates, cinnamates, benzophenones, 2-phenylbenzimidazole-5-sulphonic acid and its salts, urocanic acid and its salts, ethyl urocanate, 2-phenyl-5-methyl-benzoxazole, 2-(2'-hydroxy-5-'-methyl-phenyl)benzotriazole, 2-(2'-hydroxy-5'-tert-octyl-phenyl)benzotriazole, sodium 3,4-dimethyoxy-phenyl-glyoxylate, dibenzalazine, dianisoylmethane, 4-isopropyldibenzoylmethane, 4-tert-butyl-4'-methoxydibenzoylmethane, 3-benzylidene-dl-camphor, 3-(4'-methylbenzylidene-dl-camphor, 3-(4'-sulphobenzylidene)-camphoric acid and its salts, 3-(3'-sulpho-4'-methylbenzylidene) camphoric acid and its salts, 4-(2-oxo-3-bornylidenemethyl)phenyltrimethylammonium methyl sulphate, benzene-1,4-bis(3-methylidene-10-camphorsulphonic) acid and its salts, N-(2-ethylhexyl)-4-(3'-methylidenecamphor)benzenesulphonamide, N-(2-ethylhexyl)-3-[(3'-methoxy-4'-n-butoxy)benzylidene]-10-camphorsulphonamide, N-(2-ethylhexyl)-3-benzylidene-10-camphorsulphonamide, methyleugenol, guanine, digalloyl trioleate, 5-(3,3-dimethyl-2-norbornylidene)-3-penten-2-one, the homopolymer of 3-[3'-(acrylamidomethyl)-benzylidene]-dl-camphor of MW less than 20,000 and the copolymer of 2-[2'-hydroxy-5'-tert-octyl)phenyl]-2H-benzotriazole and butyl vinyl ether.

10. Cosmetic composition according to claim 1, which is in the form of a suspension or dispersion in solvents or fats, in the form of an emulsion or in the form of an ointment, a gel, a solid stick, or an aerosol.

11. Cosmetic composition according to claim 10, which contains cosmetic adjuvants selected from the group consisting of thickeners, emollients, moisturizers, surfactants, preservatives, sequestering agents, antioxidants, antifoams, oils, waxes, lanolin, perfumes, propellents, colorants and vitamins.

12. Cosmetic composition according to claim 10 which is in the form of a water-in-oil emulsion comprising, in addition to the infrared-reflecting agent, fatty alcohols, fatty acid esters, fatty acids, lanolin, natural or synthetic oils or waxes, and emulsifiers, in the presence of water.

13. Transparent cosmetic composition for protecting the human epidermis against infrared radiation, which comprises, in a cosmetically acceptable vehicle, an effective amount of at least one substance that reflects infrared radiation, dispersible in said vehicle, possessing a reflectance (R) of infrared radiation equal to at least 45%, and of which a 2% strength dispersion in vaseline possesses an optical transmission in the visible of at least 85%, selected from the group consisting of diatomite, hollow glass microspheres of particle size less than 100 microns, and zirconium powder-covered microparticles of particle size less than 8 microns.

14. Process for protecting the human epidermis against infrared radiation which consists in applying on the skin an amount effective for reflecting infrared radiation of a transparent cosmetic composition comprising, in a cosmetically-acceptable vehicle, an amount effective for reflecting infrared radiation of at least one substance dispersible in said cosmetic vehicle possessing a reflectance (R) of infrared radiation equal to at least 45% and of which a 2% strength dispersion in vaseline possesses an optical transmission in the visible of at least 85%, said substance being selected from the group consisting of diatomite, hollow glass microspheres of size less than 100 microns, bismuth oxychloride of particle size less than 75 microns and zirconium powder-covered ceramic microparticles of particle size less than 8 microns.

15. A process in accordance with claim 14 wherein said substance possesses a reflectance (R) equal to at least 55% and of which a 2% strength dispersion in vaseline possesses an optical transmission in the visible of at least 90%.

16. A process in accordance with claim 14 in which said substance is selected from the group consisting of diatomite, hollow glass microspheres of particle size less than 75 microns, bismuth oxychloride of average particle size from 6 to 15 microns and zirconium-powder covered ceramic microparticles having a particle size of 4 to 5 microns.

17. A process in accordance with claim 14 in which said composition comprises 0.5 to 20%, based on the total weight of the composition, of said infrared-reflecting substance.

18. A process in accordance with claim 17 in which said composition comprises 1 to 10% by weight of said infrared-reflecting substance.

19. A process in accordance with claim 18 in which said composition comprises 1-3% by weight of said infrared-reflecting substance.

20. A process in accordance with claim 14 in which said composition further contains UV-screening agents consisting of lipid-soluble or water-soluble UV-A, UV-B, or broad-band screening agents which are compatible with said infrared-reflecting substance.

21. A process in accordance with claim 20 in which said composition contains 0.5 to 20% by weight of the total composition of at least one UV-A, UV-B or broad-band screening agent.

22. A process in accordance with claim 14 in which said composition is in the form of a suspension or dispersion in solvents or fats, an emulsion, an ointment, a gel, a solid stick, or an aerosol.

23. A process in accordance with claim 21 in which said UV-screening agent is selected from the group consisting of p-aminobenzoic acid and its esters, salicylates, cinnamates, benzophenones, 2-phenylbenzimidazole-5-sulphonic acid and its salts, urocanic acid and its salts, ethyl urocanate, 2-phenyl-5-methylbenzoxazole, 2-(2'-hydroxy-5-'-methylphenyl)benzotriazole, 2-(2'-hydroxy-5'-tert-octylphenyl)benzotriazole, sodium 3,4-dimethyoxyphenylglyoxylate, dibenzalazine, dianisoylmethane, 4-isopropyldibenzoylmethane, 4-tert-butyl-4'-methoxydibenzoylmethane, 3-benzylidene-dl-camphor, 3-(4'-methylbenzylidene-dl-camphor, 3-(4'-sulphobenzylidene)camphoric acid and its salts, 3-(3'-sulpho-4'-methylbenzylidene) camphoric acid and its salts, 4-(2-oxo-3-bornylidenemethyl)phenyltrimethylammonium methyl sulphate, benzene-1,4-bis(3-methylidene-10-camphorsulphonic) acid and its salts, N-(2-ethylhexyl)-4-(3'-methylidenecamphor)benzenesulphonamide, N-(2-ethylhexyl)-3-[(3'-methoxy-4'-n-butoxy)benzylidene]-10-camphorsulphonamide, N-(2-ethylhexyl)-3-benzylidene-10-camphorsulphonamide, methyleugenol, guanine, digalloyl trioleate, 5-(3,3-dimethyl-2-norbornylidene)-3-penten-2-one, the homopolymer of 3-[3'-(acrylamidomethyl)benzylidene]-dicamphor of MW less than 20,000 and the copolymer of 2-[2'-hydroxy-5'-tert-octyl)phenyl]-2H-benzotriazole and butyl vinyl ether.

* * * * *